United States Patent
Zakhary

(10) Patent No.: US 10,993,710 B2
(45) Date of Patent: May 4, 2021

(54) SYNDESMOSIS CONSTRUCT

(71) Applicant: Wright Medical Technology, Inc., Memphis, TN (US)

(72) Inventor: Beniamin Zakhary, Marietta, GA (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 0 days.

(21) Appl. No.: 15/738,771

(22) PCT Filed: Dec. 19, 2017

(86) PCT No.: PCT/US2017/067330
§ 371 (c)(1),
(2) Date: Dec. 21, 2017

(87) PCT Pub. No.: WO2018/118931
PCT Pub. Date: Jun. 28, 2018

(65) Prior Publication Data
US 2020/0038010 A1 Feb. 6, 2020

Related U.S. Application Data

(60) Provisional application No. 62/437,390, filed on Dec. 21, 2016.

(51) Int. Cl.
*A61B 17/04* (2006.01)
(52) U.S. Cl.
CPC .. *A61B 17/0401* (2013.01); *A61B 2017/0404* (2013.01); *A61B 2017/0414* (2013.01); *A61B 2017/0438* (2013.01); *A61B 2017/0445* (2013.01); *A61B 2017/0458* (2013.01)

(58) Field of Classification Search
CPC ........ A61B 17/0401; A61B 2017/0404; A61B 2017/0414; A61B 2017/0438; A61B 2017/0445; A61B 2017/045; A61B 2017/0458; A61B 2017/0459
See application file for complete search history.

(56) References Cited

U.S. PATENT DOCUMENTS

| | | | |
|---|---|---|---|
| 5,383,905 A | 1/1995 | Golds et al. |
| 5,409,499 A | 4/1995 | Yi |
| 5,571,175 A | 11/1996 | Vanney et al. |
| 5,843,178 A | 12/1998 | Vanney et al. |
| 7,442,202 B2 | 10/2008 | Dreyfuss |
| 8,062,334 B2 | 11/2011 | Green et al. |

(Continued)

*Primary Examiner* — Eric S Gibson
(74) *Attorney, Agent, or Firm* — Duane Morris LLP

(57) ABSTRACT

A knotless button includes a body defining a proximal portion and a distal portion. The body further defines an internal cavity and a first loop opening extending from the internal cavity to an outer surface of the body. A locking insert is slideably positioned within the internal cavity. The locking insert defines a second loop opening extending from a first side of the locking insert to a second side of the locking insert. The locking insert is slideably moveable from a first position to a second position within the internal cavity. A flexible strand defines a first adjustable loop extending through the first loop opening and the second loop opening. The locking insert is slideably moveable from a first position configured to allow adjustment of the first adjustable loop to a second position configured to lock the first adjustable loop.

11 Claims, 20 Drawing Sheets

(56) References Cited

U.S. PATENT DOCUMENTS

| | | | |
|---|---|---|---|
| 8,202,295 B2* | 6/2012 | Kaplan | A61B 17/0401 606/232 |
| 8,282,674 B2 | 10/2012 | Gelfand | |
| 8,317,825 B2 | 11/2012 | Stone | |
| 8,545,535 B2 | 10/2013 | Hirotsuka et al. | |
| 9,023,083 B2 | 5/2015 | Foerster et al. | |
| 9,023,088 B2* | 5/2015 | Voisard | A61L 31/022 606/313 |
| 9,034,014 B2 | 5/2015 | Catania et al. | |
| 9,039,739 B2 | 5/2015 | Rohlinger et al. | |
| 9,131,937 B2* | 9/2015 | Chan | A61B 17/0401 |
| 9,138,221 B2* | 9/2015 | Hawkins | A61B 17/0401 |
| 9,345,467 B2* | 5/2016 | Lunn | A61B 17/0401 |
| 9,357,996 B2* | 6/2016 | Voisard | A61B 17/866 |
| 9,924,935 B2* | 3/2018 | Housman | A61B 17/0401 |
| 9,936,939 B2* | 4/2018 | Nguyen | A61B 17/0401 |
| 10,426,459 B2* | 10/2019 | Fallin | A61B 17/885 |
| 10,548,585 B2* | 2/2020 | Chan | A61B 17/0401 |
| 10,675,014 B2* | 6/2020 | Chan | A61B 17/0401 |
| 2003/0065331 A1* | 4/2003 | Donnelly | A61B 17/0401 606/232 |
| 2003/0236555 A1 | 12/2003 | Thornes | |
| 2004/0138706 A1* | 7/2004 | Abrams | A61B 17/0401 606/232 |
| 2005/0055052 A1* | 3/2005 | Lombardo | A61B 17/0487 606/232 |
| 2006/0282081 A1* | 12/2006 | Fanton | A61B 17/0401 606/232 |
| 2007/0260259 A1* | 11/2007 | Fanton | A61B 17/0401 606/99 |
| 2008/0033486 A1* | 2/2008 | Whittaker | A61B 17/0469 606/232 |
| 2008/0275469 A1* | 11/2008 | Fanton | A61B 17/0401 606/139 |
| 2010/0063542 A1* | 3/2010 | van der Burg | A61B 17/0401 606/232 |
| 2010/0262185 A1* | 10/2010 | Gelfand | A61F 2/0811 606/232 |
| 2012/0059429 A1* | 3/2012 | Voisard | A61L 31/14 606/313 |
| 2012/0123474 A1 | 5/2012 | Zajac et al. | |
| 2013/0123842 A1* | 5/2013 | Chan | A61B 17/0401 606/232 |
| 2013/0131723 A1* | 5/2013 | Snell | A61B 17/0401 606/232 |
| 2013/0267998 A1* | 10/2013 | Vijay | A61B 17/0401 606/232 |
| 2014/0114352 A1 | 4/2014 | Allen | |
| 2014/0194907 A1* | 7/2014 | Bonutti | A61B 17/0401 606/151 |
| 2016/0030034 A1* | 2/2016 | Graul | A61B 17/0485 606/232 |
| 2017/0231617 A1* | 8/2017 | Levinsohn | A61B 17/0401 606/232 |
| 2018/0008256 A1* | 1/2018 | Fallin | A61B 17/0485 |
| 2019/0216455 A1* | 7/2019 | Nadim | A61B 17/0401 |
| 2020/0038010 A1* | 2/2020 | Zakhary | A61B 17/683 |

* cited by examiner

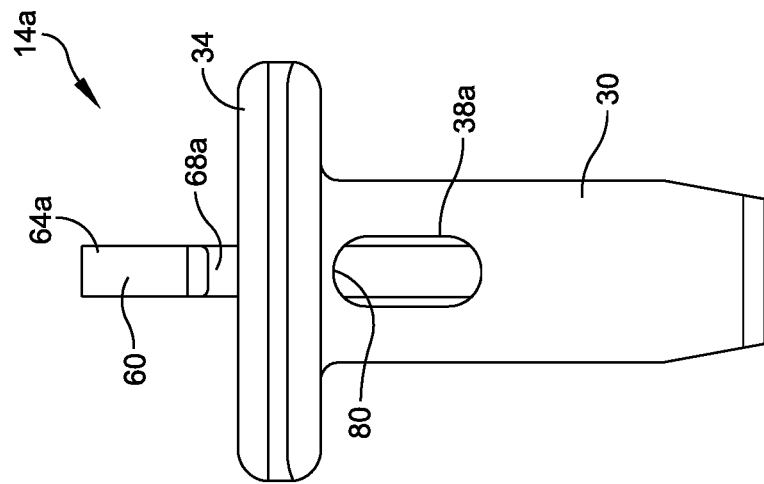
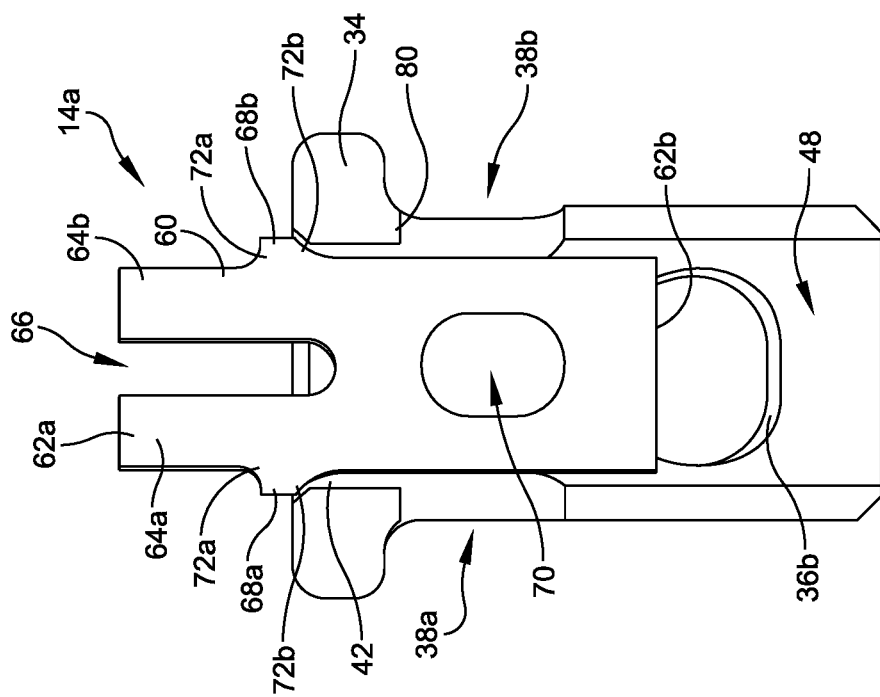

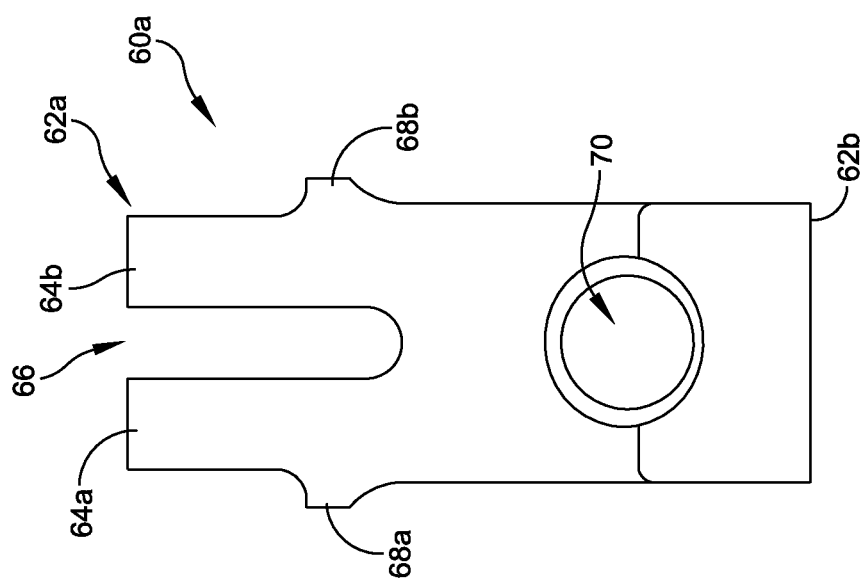

SYNDESMOSIS CONSTRUCT

CROSS-REFERENCE TO RELATED APPLICATIONS

This application is a national phase entry under 35 U.S.C. 371 of international patent application No. PCT/US17/67330, filed Dec. 19, 2017, which claims benefit to U.S. Provisional Application Ser. No. 62/437,390, filed Dec. 21, 2016, entitled "SYNDESMOSIS CONSTRUCT," the entireties of which are incorporated herein by reference.

BACKGROUND

Various injuries include separation of soft tissue from one or more bones and/or separation of bones from normally anatomical correct positioning. Maintaining the bones in the correct anatomical positions during healing is important to provide proper soft tissue reattachment and proper bone healing. For example, during syndesmosis repair, a first bone and a second bone must be maintained in a fixed position to allow the connective tissue to refuse.

Current suture systems include one or more knots for maintaining sutures in a fixed position. Knots formed on the sutures can cause irritation during healing and may be subject to tearing due to friction or other forces applied to the knot. Current systems further require surgeons to form knots during surgery. Such systems are prone to failure and increase time of surgery.

SUMMARY

In various embodiments, a knotless button is disclosed. The knotless button includes a body defining a proximal portion and a distal portion. The body further defines an internal cavity and a first loop opening extending from the internal cavity to an outer surface of the body. A locking insert is slideably positioned within the internal cavity. The locking insert defines a second loop opening extending from a first side of the locking insert to a second side of the locking insert. The locking insert is slideably moveable from a first position to a second position within the internal cavity. A flexible strand defines a first adjustable loop extending through the first loop opening and the second loop opening. The locking insert is slideably moveable from a first position configured to allow adjustment of the first adjustable loop to a second position configured to lock the first adjustable loop.

In various embodiments, a knotless button is disclosed. The knotless button includes a body defining a proximal portion and a distal portion. The body defines an internal cavity including at least one first locking feature. A locking insert is slideably receivable within the internal cavity. The locking insert defines a first loop opening extending from a first side to a second side. The locking insert is slideably moveable from a first position to a second position within the internal cavity. The locking insert is configured to receive a flexible strand defining a first adjustable loop through the first loop opening. The locking insert includes at least one second locking feature. The at least one first locking feature and the at least one second locking feature are configured to selectively couple to prevent movement of the locking insert with respect to the body.

In various embodiments, a method of coupling a first bone and a second bone is disclosed. The method includes the step of forming a bone tunnel through a first bone and a second bone. A knotless button is inserted at least partially through the bone tunnel. The knotless button includes a body defining a proximal portion and a distal portion. The distal portion defining an internal cavity and a first loop opening. A locking insert is slideably positioned within the internal cavity and defining a second loop opening extending from a first side to a second side. A flexible strand defines a first adjustable loop extending through the first loop opening and the second loop opening. The first adjustable loop is coupled to the second bone. The first adjustable loop is adjusted to position the first bone and the second bone. Adjusting the first adjustable loop to slideably transition the locking insert from a first position in which the first adjustable loop is adjustable to a second position in which the first adjustable loop is locked.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 2B is a cross-section of the knotless button of FIG. 2A, in accordance with some embodiments.

FIG. 2C is a side-view of the knotless button of FIG. 2A, in accordance with some embodiments.

FIG. 8 illustrates a self-tightening insert configured to be received within a knotless button, in accordance with some embodiments.

DETAILED DESCRIPTION

Figure 1:
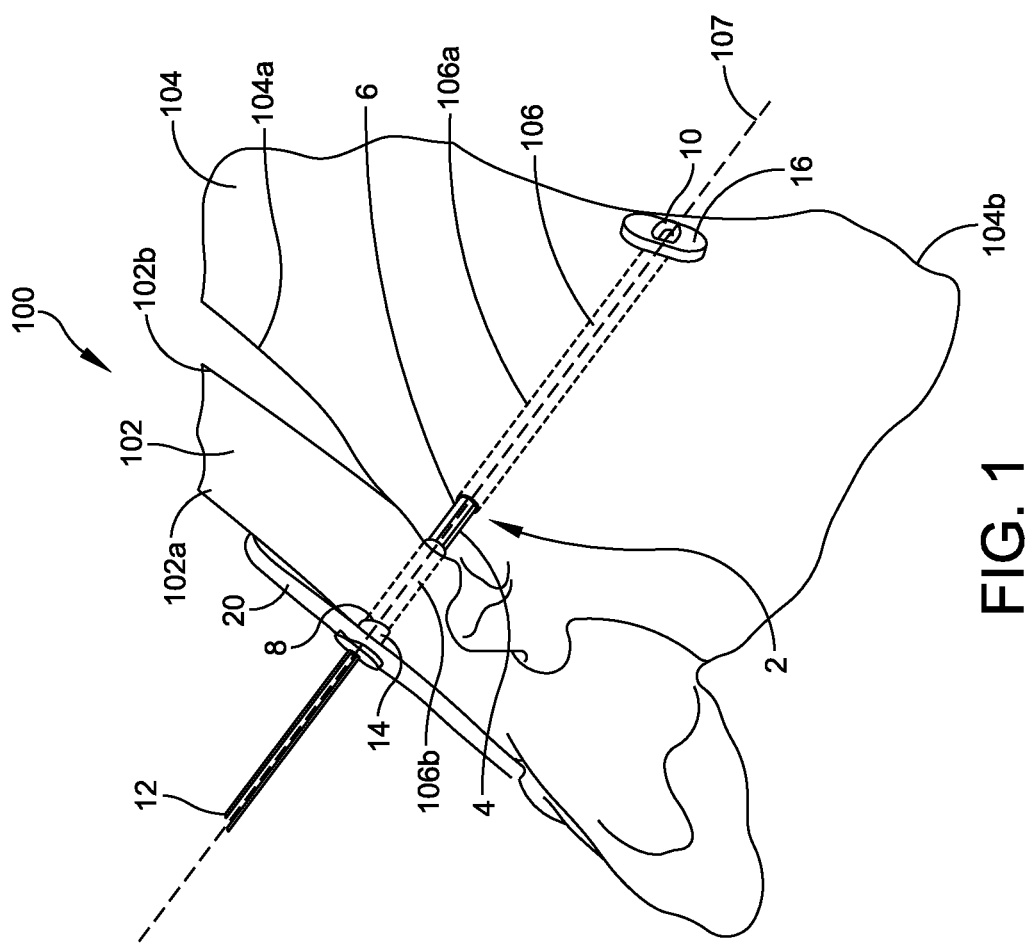
FIG. 1 illustrates a surgical site including a first bone and a second bone coupled by an anchoring construct, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

In various embodiments, an anchoring construct including a flexible strand defining at least one adjustable loop is disclosed. The adjustable loop is coupled to a knotless button at a first end. The knotless button includes a body defining an internal cavity configured to receive a locking insert therein. The body of the knotless button and the locking insert each define a loop channel. The adjustable loop extends through the loop channel and is further looped beneath a distal end of the locking insert. The locking insert is configured to transition from a first position in which the adjustable loop can be adjusted and a second position in which the adjustable loop is locked. In some embodiments, a second end of the adjustable loop is coupled to a flat button.

FIG. 1 illustrates a surgical site 100 including a first bone 102 and a second bone 104 coupled by an anchoring construct 2. The anchoring construct 2 is configured to limit the movement and/or position of the first bone 102 with respect to the second bone 104. The anchoring construct 2 includes a flexible strand 4 defining at least one loop 6 extending from a proximal end 8 to a distal end 10. The flexible strand 4 can include any suitable material, such as, for example, one or more sutures, threads, ribbons, and/or other suitable flexible material. In some embodiments, an adjustment portion 12 of the flexible strand 4 extends proximally from the at least one loop 6. The adjustment portion 12 is configured to provide adjustment (e.g., lengthening/shortening/tightening/loosening) of the at least one flexible loop 6.

In some embodiments, the proximal end 8 of the at least one adjustable loop 6 is coupled to a knotless button 14. The knotless button 14 includes one or more openings for receiving the at least one loop 6, as discussed in more detail below. For example, as discussed in more detail with respect to FIGS. 4A-5E, in some embodiments, the knotless button 14 includes a body defining a first loop opening and a second loop opening configured to receive the at least one flexible loop 6 therethrough. The knotless button 14 anchors the proximal end 8 of the at least one flexible loop 6 to a first side 102a (such as, for example, a lateral side) of the first bone 102. In some embodiments, a locking insert is positioned within the inner cavity (see FIG. 2) and is configured to maintain the adjustable loop 6 at a preselected length.

In some embodiments, a distal end 10 of the at least one flexible loop 6 is coupled to a flat button 16. The flat button 16 includes one or more openings configured to receive a portion of a flexible loop 6 therethrough. The at least one flexible loop 6 is looped around and/or through a portion of the flat button 16. The flat button 16 anchors the distal end 10 of the at least one flexible loop 6 to a medial side 104b of the second bone 104.

In some embodiments, the knotless button 14 is coupled to a bone plate 20. The bone plate 20 can be coupled to the first side 102a of the first bone 102. The bone plate 20 includes a body 22 extending between a first (or bone-contact) surface 24 and an opposing second (or outer) surface 26 (see FIGS. 11A-11C). The body 22 has a predetermined thickness. In some embodiments, the body 22 defines one or more anchor holes and/or one or more fastener holes. For example, in the illustrated embodiment, the body 22 defines at least one button hole 28 sized and configured to receive a knotless button (e.g., the knotless button 14) at least partially therethrough (see FIGS. 11A-11C). The button hole 28 can define a countersink (see FIGS. 11A-11C) configured to receive a proximal portion of the knotless button 14. In some embodiments, the bone plate 20 further defines one or more fastener holes 29 configured to receive a fastener therethrough to couple the bone plate 20 to a first bone 102 (see FIG. 10).

In some embodiments, the adjustable loop 6 extends from the first side 102a of the first bone 102 to a second side 104b of the second bone 104 through a bone tunnel 106 defined in the first and second bones 102, 104. The bone tunnel 106 includes a first portion 106a extending from the first side 102a to a second side 102b of the first bone 102 and a second portion 106b extending from a first side 104a to the second side 104b of the second bone 104. The bone tunnel 106 can be formed using any suitable surgical device, such as, for example, a drill, a k-wire, an impactor, a needle, and/or any other suitable device.

In some embodiments, the bone tunnel 106 has a diameter sufficient to allow the flat button 16 to pass through the bone tunnel 106 in a first configuration. The flat button 16 may include an oblong (or elliptical) shape having a first diameter 96a greater than a second diameter 96b (see FIG. 12). When the oblong flat button 16 is positioned at a first orientation (such as with the long axis 96a of the elliptical shape parallel to an axis 107 of the bone tunnel 106), the flat button 16 is able to pass through the bone tunnel 106. When the flat button 16 is positioned at a second orientation (e.g., with the long axis 96a of the elliptical shape substantially perpendicular to the axis 107 of the bone tunnel 106), the flat button 16 is not able to pass through the bone tunnel 106. In other embodiments, the bone tunnel 106 has a diameter sufficient to allow passage of an adjustable loop 6 and one or more passage elements, such as a needle but less than either of the diameters 96a, 96b of the flat button 16. The flat button 16 can be coupled to one or more of the adjustable loops 6 after insertion of the adjustable loop 6 through the bone tunnel 106. In some embodiments, the adjustable loop 6 is passed through the bone tunnel 106 using one or more elements, such as, for example, a needle 86 (see FIG. 10).

The adjustable loop 6 is adjusted (e.g., shortened/lengthened) to position the first bone 102 and the second bone 104 in a predetermined spaced relationship. In some embodiments, the adjustment portion 12 of the flexible strand 4 extends through an opening formed in a proximal end of the knotless button 14. The adjustment portion 12 can be manipulated (e.g., pulled) to shorten/tighten the adjustable loop 6 to position the first bone 102 and the second bone 104. When the first bone 102 and the second bone 104 are in the predetermined spaced arrangement, the locking insert can be locked to prevent movement of the adjustable loop 6. For example, in some embodiments, the locking insert locks the adjustable loop 6 at a selected length to limit the movement of the first and second bones 102, 104 to a predetermined range of motion.

Figure 2A:
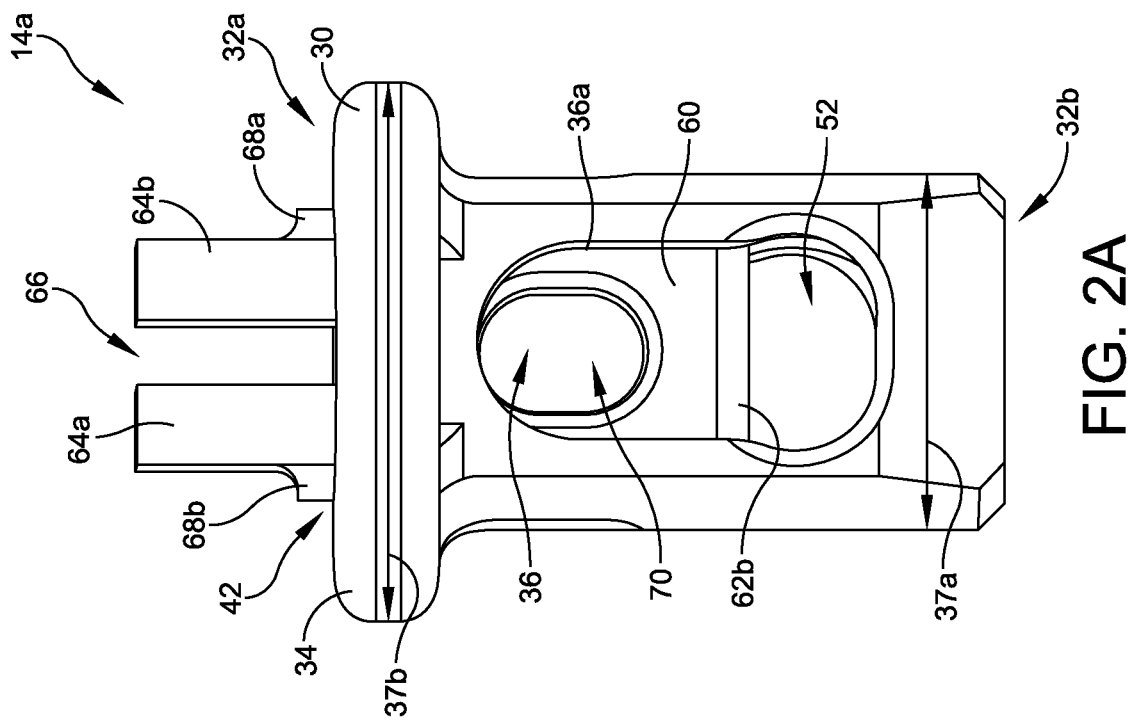
FIG. 2A illustrates a knotless button having a locking insert in a first position, in accordance with some embodiments.

FIGS. 2A-2C illustrate a knotless button 14a, in accordance with some embodiments. The knotless button 14a is similar to the knotless button 14 discussed above, and similar description is not repeated herein. The knotless button 14a includes a body 30 extending between a proximal end 32a and a distal end 32b. The body 30 can have any suitable shape, such as, for example, a cylindrical shape, a rectangular shape, a pyramidal shape, and/or any other suitable shape. In some embodiments, the body 30 has a first diameter 37a. Further, the body 30 includes a proximal cap 34 located at a proximal end 32a of the body 30. In some embodiments, the proximal cap 34 has a second diameter 37b that is greater than the first diameter 37a. It should be noted that the proximal cap 34 may be integral with the body 30 (e.g., a monolithic construct). In other embodiments, the proximal cap 34 may be provided as a separate component or piece, connectively attached or received by the body 30.

In some embodiments, the body 30 defines a first loop opening 36a and a second loop opening 36b. The loop openings 36a, 36b are sized and configured to receive a portion of the adjustable loop 6 therethrough. The adjustable loop 6 extends distally from at least one of the loop openings 36a, 36b. In some embodiments, the loop openings 36a, 36b define a loop channel 36 extending through the body 30 of the knotless button 14a.

The body 30 defines an internal cavity 48 sized and configured to receive a locking insert 60 therein. In some embodiments, the internal cavity 48, extends along a length of the body 30, from the proximal end 32a to the distal end 32b. The proximal end 32a and/or the distal end 32b can define a closed end or an open end. For example, in some embodiments, a first opening 42 can be defined by and extend through the proximal cap 34 to the internal cavity 48 such that the internal cavity 48 defines a channel extending from the first opening 42 to the distal end of the body 32b. The locking insert 60 can be slideably received within the internal cavity 48 by inserting the locking insert 60 through the first opening 42. In some embodiments, where the body comprises a separate proximal cap 34, the locking insert 60 can be inserted into the internal cavity 48 prior to coupling the proximal cap 34 to the body 30. The first opening 42 may be a longitudinal opening configured to match a cross-sectional area of the internal cavity 48 and/or a cross-sectional area of the locking insert 60.

Figure 3A:
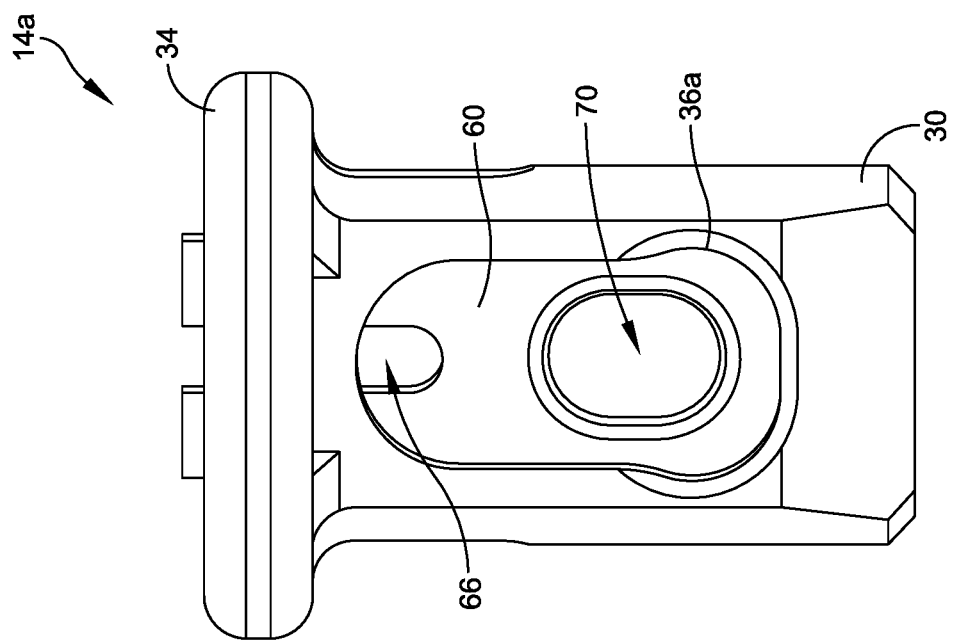
FIG. 3A illustrates the knotless button of FIGS. 2A-2C having a locking insert in a second position, in accordance with some embodiments.
Figure 3C:
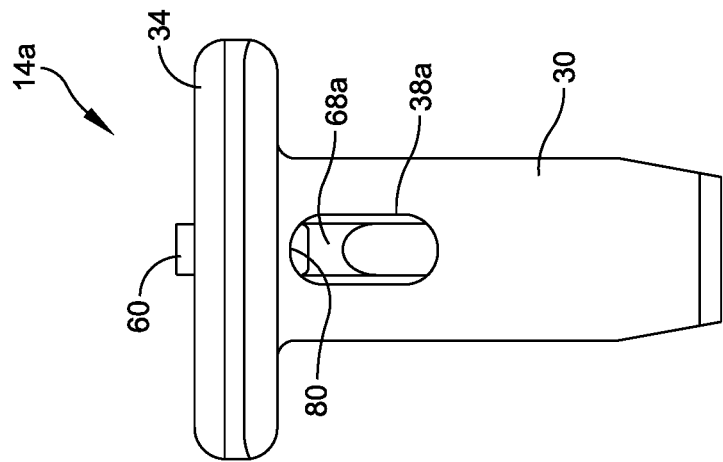
FIG. 3C is a side-view of the knotless button of FIG. 3A, in accordance with some embodiments.
Figure 3B:
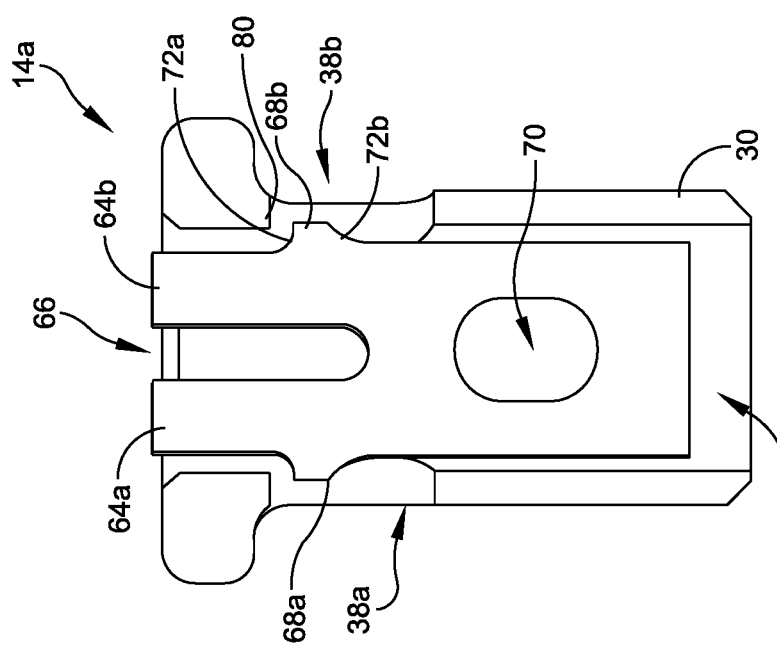
FIG. 3B is a cross-section of the knotless button of FIG. 3A, in accordance with some embodiments.
Figure 4:
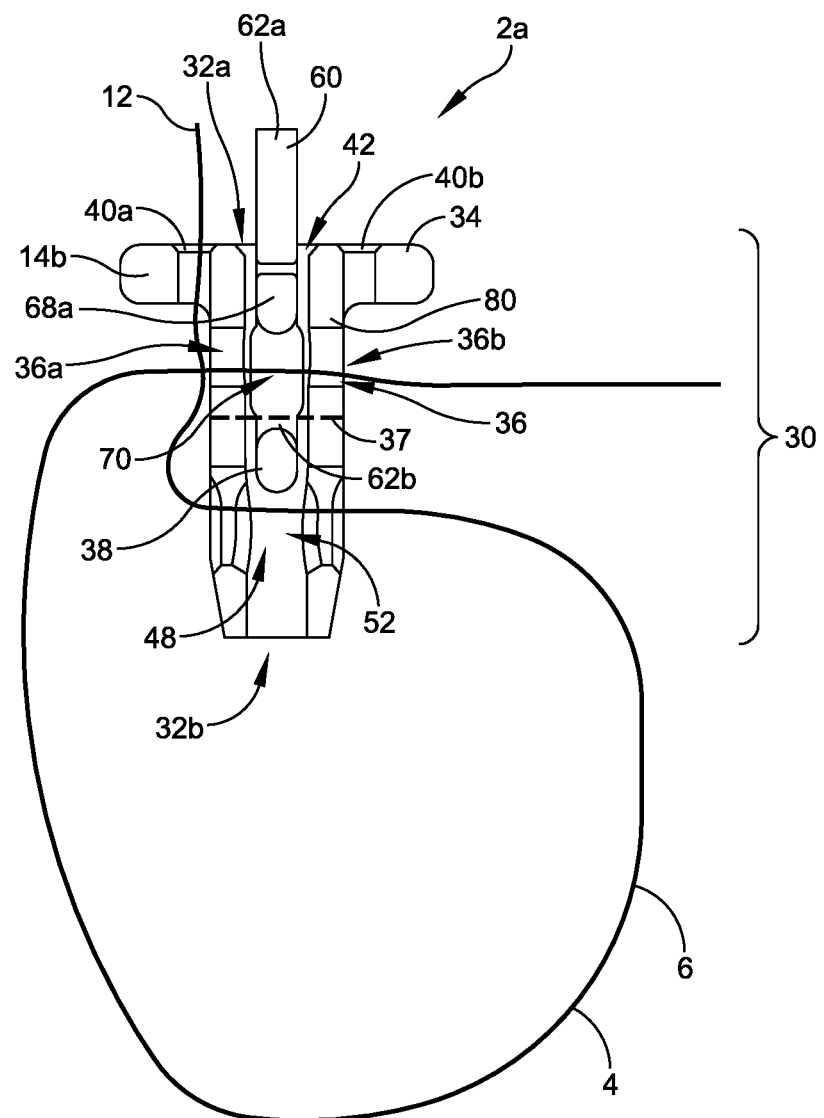
FIG. 4 illustrates an anchoring construct including the knotless button of FIGS. 2A-3C having a first adjustable loop coupled thereto, in accordance with some embodiments.

In some embodiments, the locking insert 60 is slideably moveable within the internal cavity 48 along a vertical axis of the body 30 from a first (proximal) position defining a strand receiving space 52, as illustrated in FIGS. 2A-2C, to a second (distal) position in which the locking insert 60 is positioned substantially within the strand receiving space 52, as illustrated in FIGS. 3A-3C. In some embodiments, the locking insert 60 includes one or more first locking features 68a, 68b sized and configured to couple to and/or interact with second locking features 38a, 38b defined by the body 30. The first locking features 68a, 68b are configured to retain the locking insert 60 in the second position. In some embodiments, the first locking features 68a, 68b (such as tabs extending laterally from the locking insert 60) interact with a stop surface 80 when the locking insert 60 is positioned within the internal cavity 48. The stop surface 80 can be defined by the proximal cap 34 and/or the proximal end 32a of the body 30. The first locking features 68a, 68b interface with the stop surface 80 which prevents the locking insert 60 from being removed proximally from the internal cavity 48. In some embodiments, the first locking features 68a, 68b, define a flat proximal surface configured to interface with stop surface 80. In other embodiments, the first and second locking features can comprise any suitable cooperating locking features.

In some embodiments, the locking insert 60 is configured to flex or otherwise deform during insertion into and/or removal from the internal cavity 48. For example, in the illustrated embodiment, a slot 66 divides a proximal end 62a into a first prong 64a and a second prong 64b that can be flexed towards a center line of the locking insert 60 during insertion and/or removal of the locking insert 60.

In some embodiments, the body 30 comprises a material which enables the locking insert 60 to transition from the second, closed position to the first, open or unlocked position. For example, the body 30 of the knotless button 14a can be temporarily deformable to release the locking insert 60 and/or deform the first opening 42 such that the locking insert 60 can be transitioned from the second position to the first position. The body 30 may be formed from a semi-resilient material and/or semi-deformable material. Deformation of the body 30 (e.g., compressing or squeezing) releases the first locking features 68a, 68b from the second locking features 38a, 38b, allowing the locking insert 60 to transition from the second position to the first position. In some embodiments, deformation of the body 30 further allows the locking insert 60 to be removed from the internal cavity 48. Although embodiments are discussed herein including a deformable body 30, it will be appreciated that the locking insert 60 can transition from the second position to the first position using any suitable system.

In some embodiments, the locking insert 60 defines a loop opening 70 extending through the locking insert 60. The loop opening 70 is sized and configured to receive a portion of the adjustable loop 6 therethrough. When the locking insert 60 is at least partially inserted into the internal cavity 48 (e.g., is in the first position), the loop opening 70 is at least partially aligned with the loop openings 36a, 36b defined by the body 30. When the loop opening 70 is aligned with the loop openings 36a, 36b, a portion of a flexible strand, such as flexible strand 4 illustrated in FIG. 1, is passed through the first opening 36a, the loop opening 70, and the second opening 36b such that an adjustable loop is partially disposed within the loop channel 36 as defined by the loop openings 36a, 36b, 70.

In some embodiments, the locking insert 60 has a first length extending from a proximal end 62a to a distal end 62b. The first length of the locking insert 60 is less than a length of the internal cavity 48 extending from a proximal end 32a to a distal end 32b. When the locking insert 60 is positioned in a first position, a strand receiving space 52 is defined between a distal end 62b of the locking insert 60 and a distal end 32b of the internal cavity 48. The strand receiving space 52 is configured to receive a portion of an adjustable loop therein, as discussed in more detail below with respect to FIGS. 4-5.

In some embodiments, the locking insert 60 is configured to automatically transition from a first position (e.g., proximal-most position) to a second position (e.g., distal-most position) when an adjustable loop is shortened (e.g., tightened) to a predetermined length. For example, as shown in FIG. 1, the adjustable loop 6 extends from the knotless button 14 coupled to a first side 102a of a first bone to a flat button 16 coupled to a second side 104b of a second bone 104. When the adjustable loop 6 is shortened, the position of the first and second bones 102, 104 is adjusted by a force applied by the adjustable loop 6. When the force applied to the first and second bones 102, 104 by the adjustable loop 6 reaches a predetermined value, the adjustable loop 6 causes the locking insert 60 to transition from the first position to the second position and lock the adjustable loop 6 at a predetermined length.

In some embodiments, the locking insert 60 can be transitioned from the first position to the second position manually, such as, for example, using a finger, a tool, and/or any other suitable instrument. For example, when the adjustable loop 6 is shortened to a preselected length, a force is applied to the proximal end 62a of the locking insert 60 to transition the locking insert 60 to the second position. The transition force causes the first locking features 68a, 68b to interact with the second locking features 38a, 38b to lock the adjustable loop 6 at the preselected length.

FIGS. 2A-2C illustrate a knotless button 14a having the locking insert 60 positioned in the first position, in accordance with some embodiments. The first locking features 68a, 68b of the knotless button 14b includes one or more tabs extending laterally from the locking insert 60 and the second locking features 38a, 38b include slots defined by the body 30. The first locking features 68a, 68b are configured to be received within and retained by the second locking features 38a, 38b. In some embodiments, the first locking features 68a, 68b are configured to transition from a first position to a second position along a vertical axis of the body 30 (e.g., towards/away from the proximal cap 34), for example, by vertical movement caused by a pushing device or user's fingers.

In some embodiments, the first and second prongs 64a, 64b are configured to flex such that tabs 68a, 68b, can be inserted through the first opening 42 into the internal cavity 48. When the first locking features 68a, 68b are aligned with the second locking features 38a, 38b, the first and second prongs 64a, 64b return to an unflexed position, positioning the first locking features 68a, 68b within the second locking features 38a, 38b and at least partially beneath the stop surface 80.

In some embodiments, a distal portion 72b of each of the first locking features 68a, 68b are angled or curved to assist in insertion of the locking insert 60 into the internal cavity 48. For example, in some embodiments, the distal portion 72b defines a ramp configured to reduce the required flex distance (e.g., the distance that each of the first locking features 68a, 68b must travel towards a center line) for insertion of the locking insert 60 and to transfer an insertion force to the prongs 64a, 64b.

FIGS. 3A-3C illustrate the knotless button 14a having the locking insert 60 positioned in a second position, in accordance with some embodiments. As shown in FIGS. 3A-3C, the locking insert 60 is fully inserted into the internal cavity 48 in the second position such that the locking insert 60 extends through the strand receiving space 52. When the locking insert 60 is in the second position, the portion of the flexible strand 4 extending beneath the locking insert 60 is clamped or compressed and the adjustable loop 6 is maintained at the preselected length.

As shown in FIG. 3C, in some embodiments, when the locking insert 60 is positioned at a second position, the first locking elements 68a, 68b, are positioned within and/or interact with the second locking features 38a, 38b defined by the body 30. The second locking features 38a, 38b allow the prongs 64a, 64b of the locking insert 60 to return to an unflexed position. In some embodiments, a flat proximal side 72a of the first locking features 68a, 68b interact with a stop surface 80 defined by the body 30. The stop surface 80 prevents proximal movement of the locking insert 60 after insertion into the internal cavity 48.

In some embodiments, the body 30 of the knotless button 14a defines a resiliently deformable material that is configured to be temporarily deformed to release the locking insert 60 from the internal cavity 48. For example, in some embodiments, the body 30 can be squeezed or otherwise deformed to release the first locking features 68a, 68b from the second locking features 38a, 38b and allow the locking insert 60 to be removed proximally from the internal cavity 48. In other embodiments, temporary deformation of the body 30 can release first locking features 68a. 68b and second locking features 38a. 38b, reposition stop surfaces 80, and/or otherwise allow movement of the locking insert 60 from the second position to the first position. After the locking insert 60 is transitioned back to the first position, the body 30 is returned to a pre-deformed shape and the locking insert 60 can be reinserted into the internal cavity 48 to lock the adjustable loop 6 at a newly selected length.

FIG. 3 illustrates an anchoring construct 2a including a knotless button 14b coupled to an adjustable loop 6, in accordance with some embodiments. The anchoring construct 2a is similar to the anchoring construct 2 discussed in conjunction with FIG. 1 and the knotless button 14b is similar to the knotless button 14a discussed in conjunction with FIGS. 2A-3C, and similar description is not repeated herein. The anchoring construct 2a includes a flexible strand 4 defining a first adjustable loop 6. The first adjustable loop 6 is coupled to the knotless button 14b. When the locking insert 60 is positioned in the first position, the adjustable loop 6 can be shortened and/or lengthened to a preselected length. A first portion of the flexible strand 4 defining the adjustable loop 6 passes through a loop passage 36 defined by the loop openings 36a, 36b in the body 30 and the loop opening 70 in the locking insert 60. A second portion of the flexible strand 4 passes through the strand receiving space 52 below the distal end 62b of the locking insert 60. In some embodiments, an adjustment strand 12 extends proximally from the body 30 and can be manipulated (e.g., pulled) to shorten/lengthen the adjustable loop 6. When the adjustable loop 6 is adjusted to a preselected length, the locking insert 60 is transitioned to the second position with respect to the body 30.

In the second position, the locking insert 60 locks the flexible strand 4 between the locking insert 60 and the body 30 to maintain the adjustable loop 6 at a preselected length. For example, in some embodiments, the flexible strand 4 is looped through the first and second loop openings 36a, 36b and beneath the distal end 62b of the locking insert 48 such that a portion of the flexible strand 4 is positioned within strand receiving space 52. In other embodiments, additional loop openings (not shown) can be defined by the body 30 distally of the first and second loop openings 36*a*, 36*b* and the flexible strand 4 can be looped through the additional openings to define an adjustable loop 6. In some embodiments, an adjustment portion 12 of the adjustable loop 6 extends proximally through the proximal cap 32 of the knotless button 14*b*. In some embodiments, the adjustment portion 12 extends through a first adjustment hole 40*a* defined by the proximal cap 34. The adjustment portion 12 is configured to adjust the length of the adjustable loop 6. For example, in some embodiments, proximal movement of the adjustment portion 12 shortens the length (e.g., diameter) of the adjustable loop 6 and distal movement of the adjustment portion 12 lengthens the adjustable loop 6.

Figure 5:
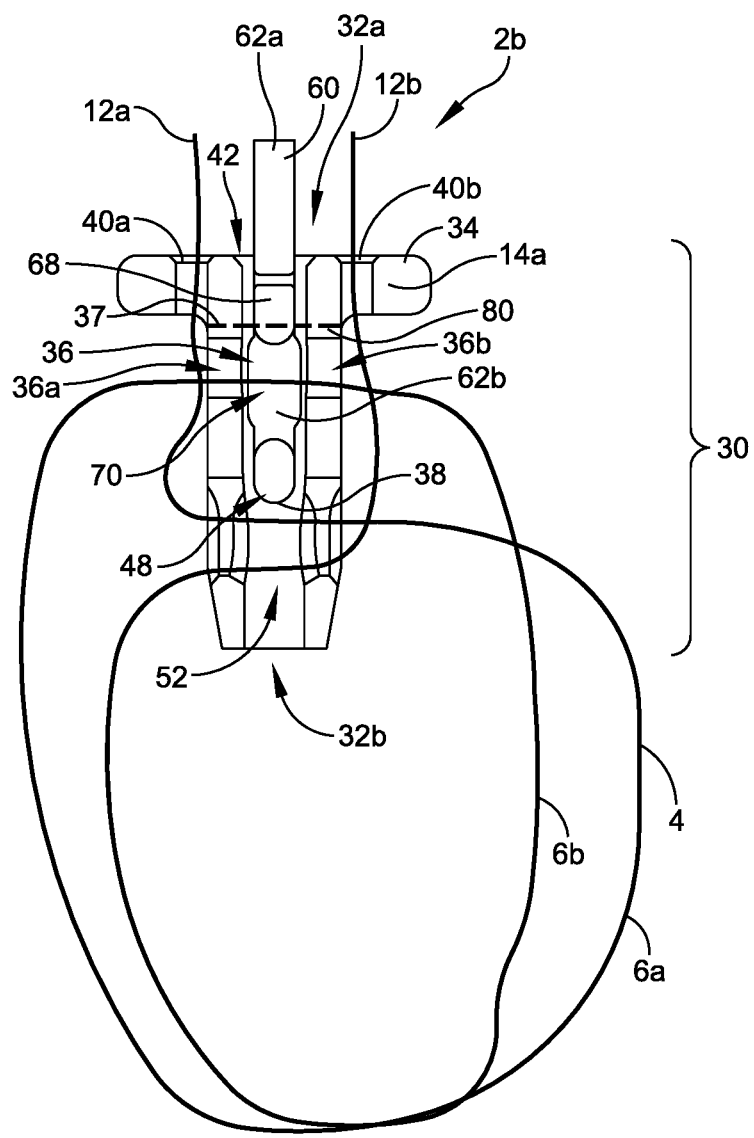
FIG. 5 illustrates an anchoring construct including the knotless button of FIGS. 2A-3C having a first adjustable loop and a second adjustable loop coupled thereto, in accordance with some embodiments.
Figure 6B:
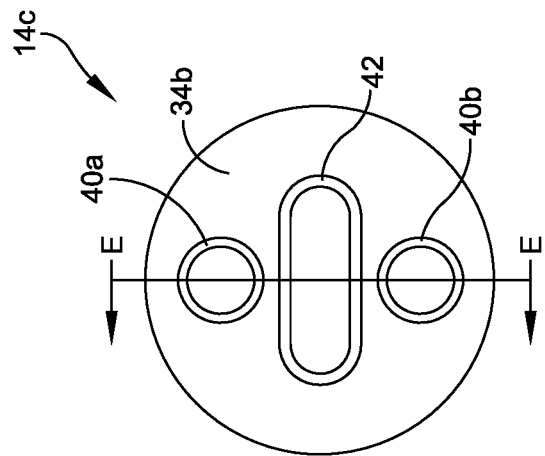
FIG. 6B illustrates a top view of the knotless button of FIG. 6A, in accordance with some embodiments.
Figure 6A:
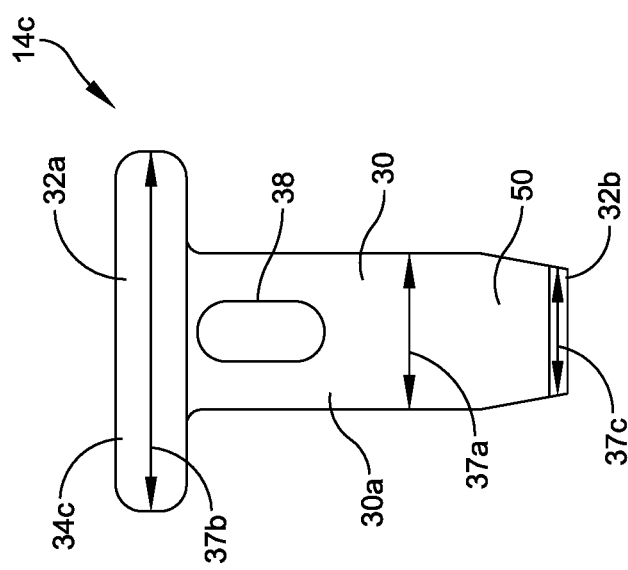
FIG. 6A illustrates a front view of a knotless button configured to receive at least one adjustable loop therethrough, in accordance with some embodiments.
Figure 6D:
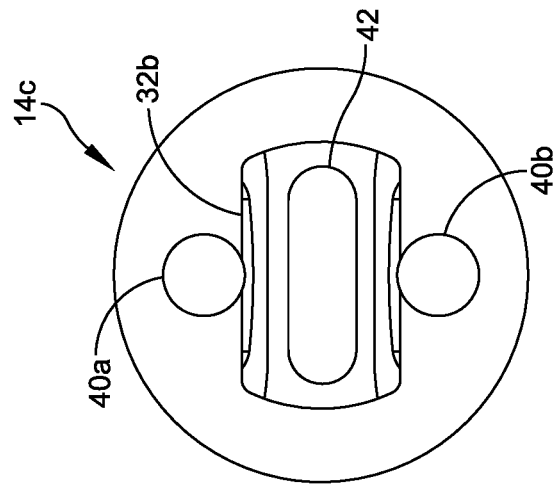
FIG. 6D illustrates a bottom view of the knotless button of FIG. 6A, in accordance with some embodiments.
Figure 6C:
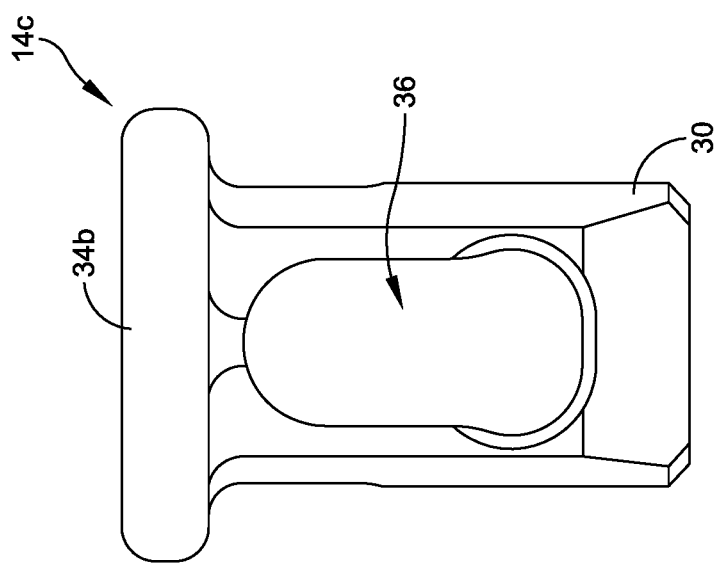
FIG. 6C illustrates a side view of the knotless button of FIG. 6A, in accordance with some embodiments.
Figure 6E:
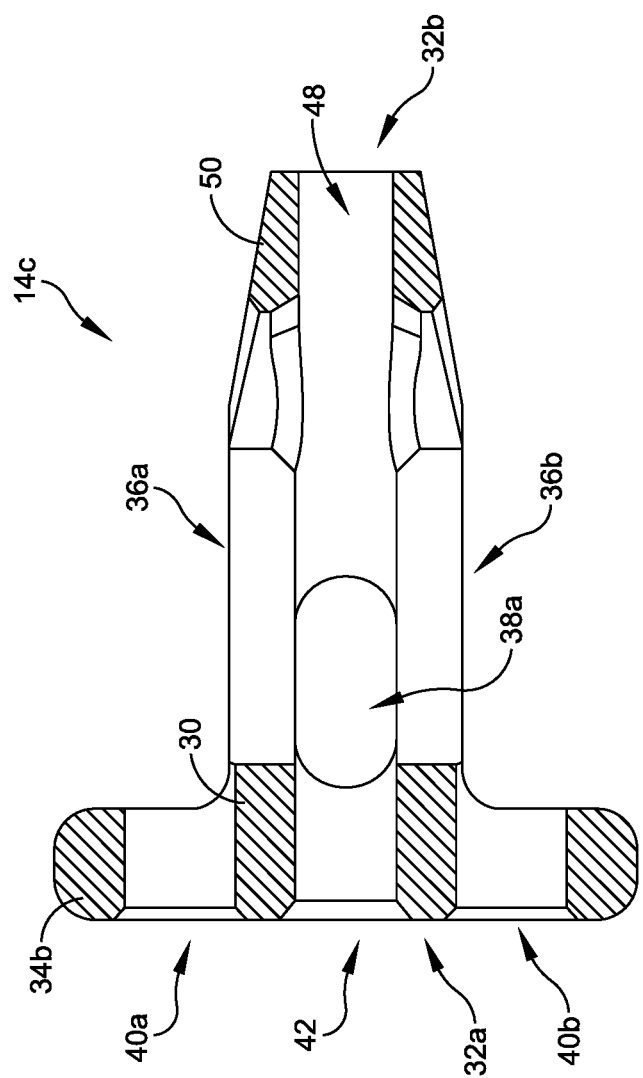
FIG. 6E illustrates a cross-sectional view of the knotless button of FIG. 6A, in accordance with some embodiments.
Figure 7B:
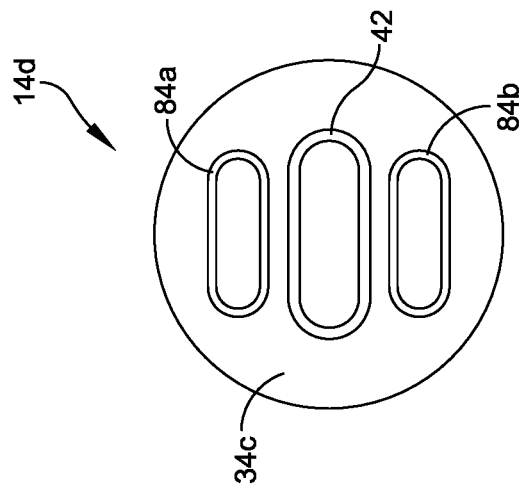
FIG. 7B illustrates a top view of the knotless button of FIG. 7A, in accordance with some embodiments.
Figure 7A:
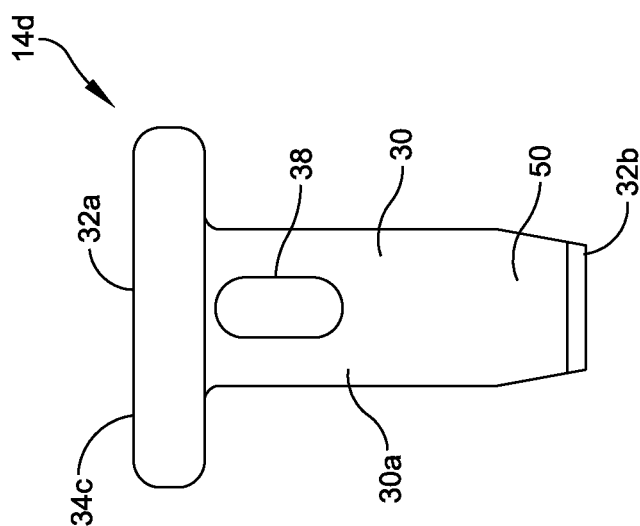
FIG. 7A illustrates a knotless button configured to receive at least one adjustable loop therethrough, in accordance with some embodiments.
Figure 7D:
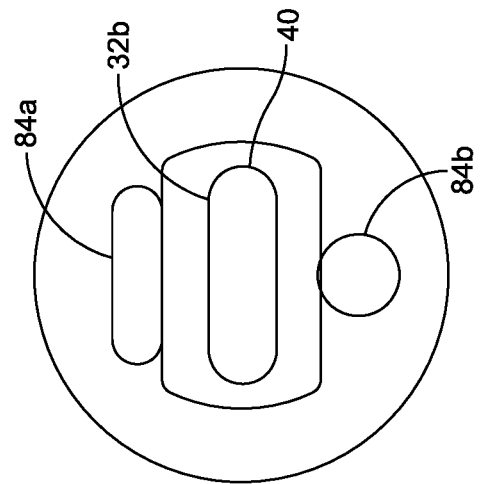
FIG. 7D illustrates a bottom view of the knotless button of FIG. 7A, in accordance with some embodiments.
Figure 7C:
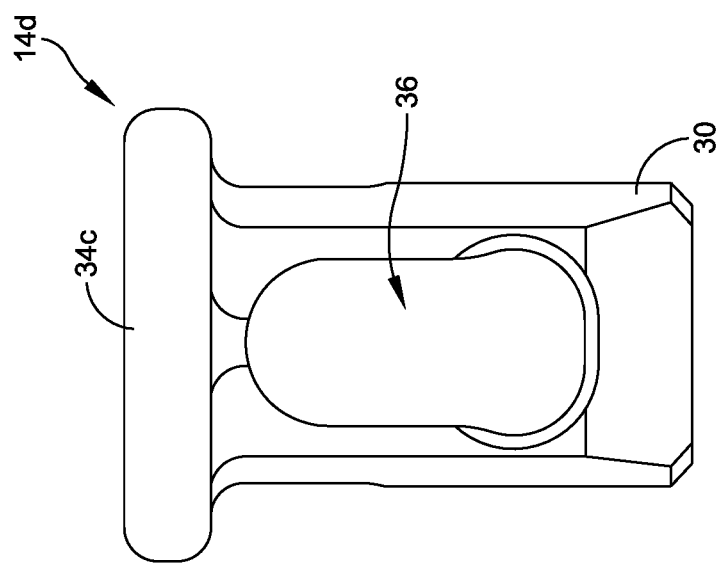
FIG. 7C illustrates a side view of the knotless button of FIG. 7A, in accordance with some embodiments.

FIG. 5 illustrates an anchoring construct 2*b* including the knotless button 14*b* coupled to first and second adjustable loops 6*a*, 6*b*, in accordance with some embodiments. The anchoring construct 2*b* is similar to the anchoring construct 2*a* discussed in conjunction with FIG. 4, and similar description is not repeated herein. The flexible strand 4 is looped multiple times through the loop passage 36 and beneath the proximal end 62*b* of the locking insert 60 to define the first and second adjustable loops 6*a*, 6*b*. A first adjustment portion 12*a* extends proximally through a first adjustment hole 40*a* and a second adjustment portion 12*b* extends proximally through a second adjustment hole 40*b*. The first adjustment portion 12*a* is configured to adjust the length of the first adjustable loop 6*a* and the second adjustment portion 12*b* is configured to adjust the length of the second adjustable loop 6*b*. Although embodiments are illustrated with one or two adjustable loops, those skilled in the art will recognize that the knotless button 14*b* can be coupled to any number of adjustable loops defined by one or more flexible strands.

FIGS. 6A-6E illustrate a knotless button 14*c*, in accordance with some embodiments. The knotless button 14*c* is similar to the knotless button 14*a* discussed above, and similar description is not repeated herein. The knotless button 14*c* includes a body 30*a* having a tapered portion 50 at a distal end 32*b*. The tapered portion 50 tapers from the first diameter 37*a* of the body 30*a* to a third diameter 37*c* defined by the distal end 32*b*. The tapered portion 50 begins distally of the one or more loop openings 34*a*, 34*b*. In some embodiments, the internal cavity 48 maintains a constant width through the tapered portion 50 and only the outer surface of the body 30*a* is tapered. In other embodiments, the internal cavity 48 tapers in conjunction with the tapered portion 50 to define a tapered internal cavity.

In some embodiments, the proximal cap 34*b* includes a plurality of adjustment openings 40*a*, 40*b*. The plurality of adjustment openings 40*a*, 40*b* are sized and configured to receive a portion of an adjustment strand 12 therethrough (see FIG. 3). In some embodiments, a first adjustment opening 40*a* and a second adjustment opening 40*b* are symmetrically positioned about the insert opening 42. In other embodiments, the adjustment openings 40*a*, 40*b* can be non-symmetrically arranged. Although embodiments are illustrated with two adjustment openings 40*a*, 40*b*, it will be appreciated that the knotless button 14*c* can include any suitable number of adjustment openings 40*a*, 40*b* each configured to receive one or more adjustment portions 12 therethrough.

FIGS. 7A-7D illustrate a knotless button 14*d*, in accordance with some embodiments. The knotless button 14*d* is similar to the knotless button 14*c* discussed in conjunction with FIGS. 6A-6E, and similar description is not repeated herein. The knotless button 14*d* includes a proximal cap 34*c* having a plurality of adjustment slots 84*a*, 84*b* instead of adjustment openings 40*a*, 40*b*. The adjustment slots 84*a*, 84*b* are sized and configured to receive a portion of an adjustment strand 12 therethrough. The adjustment slots 84*a*, 84*b* extend longitudinally to allow the adjustment strand 12 to be conveniently positioned during insertion and anchoring of the knotless button 14*d*.

FIG. 8 illustrates a locking insert 60*a*, in accordance with some embodiments. The locking insert 60*a* is similar to the locking insert 60 discussed in conjunction with FIGS. 4A-5C, and similar description is not repeated herein. The locking insert 60*a* includes a circular loop opening 70. The circular loop opening 70 is sized and configured to receive a flexible strand 4 defining at least one adjustable loop 6 therethrough. In some embodiments, the locking insert 60*a* includes a slot 66 configured to allow the first prong 64*a* and the second prong 64*b* to flex towards a center line of the locking insert 60*a*, as discussed above.

Figure 9:
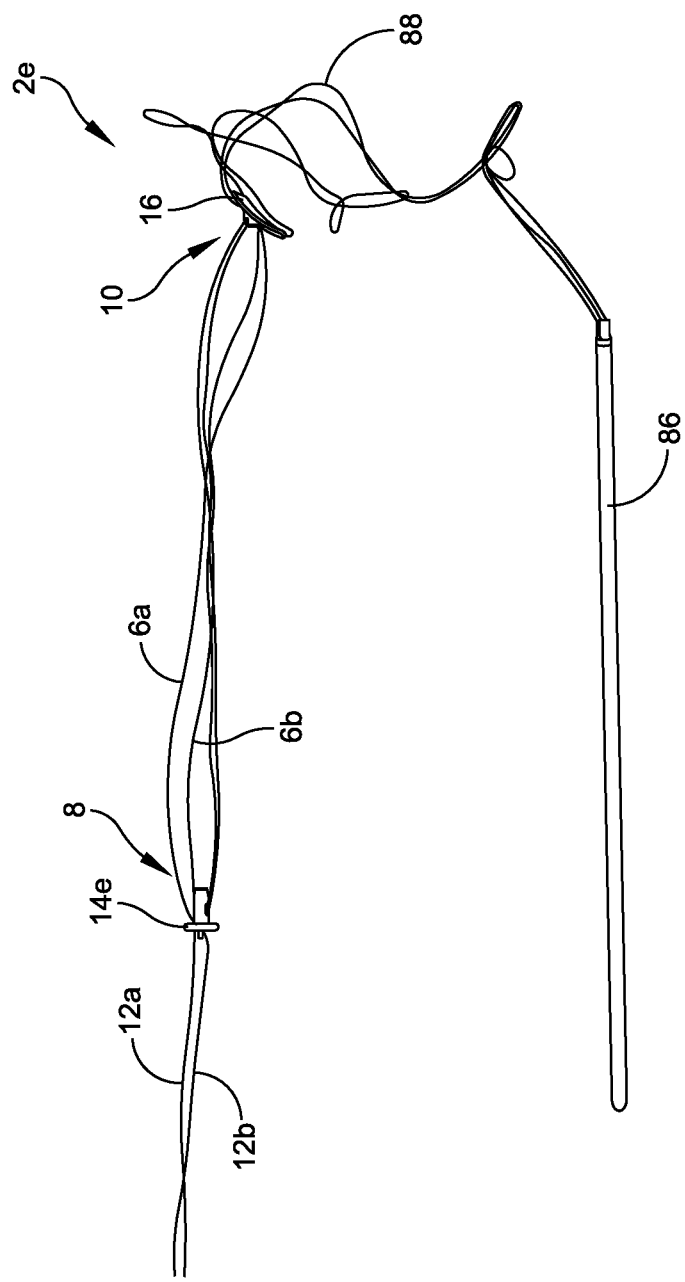
FIG. 9 illustrates an anchoring construct coupled to a needle and configured for insertion through a bone tunnel, in accordance with some embodiments.

FIG. 9 illustrates an anchoring construct 2*d* coupled to a needle and configured for insertion through a bone tunnel, in accordance with some embodiments. The anchoring construct 2*d* includes a knotless button 14*e* coupled to a plurality of adjustable loops 6*a*-6*b* at a proximal end 8. The distal end 10 of the adjustable loops 6*a*-6*b* are coupled to a flat button 16. The flat button 16 is further coupled to a needle 86 by a plurality of pull strands 88. The needle 86 is sized and configured for insertion through a bone tunnel 106 defined through at least one bone 102, 104. In some embodiments, the flat button 16 is omitted and the pull strands 88 are coupled directly to the adjustable loops 6*a*, 6*b*.

Figure 10:
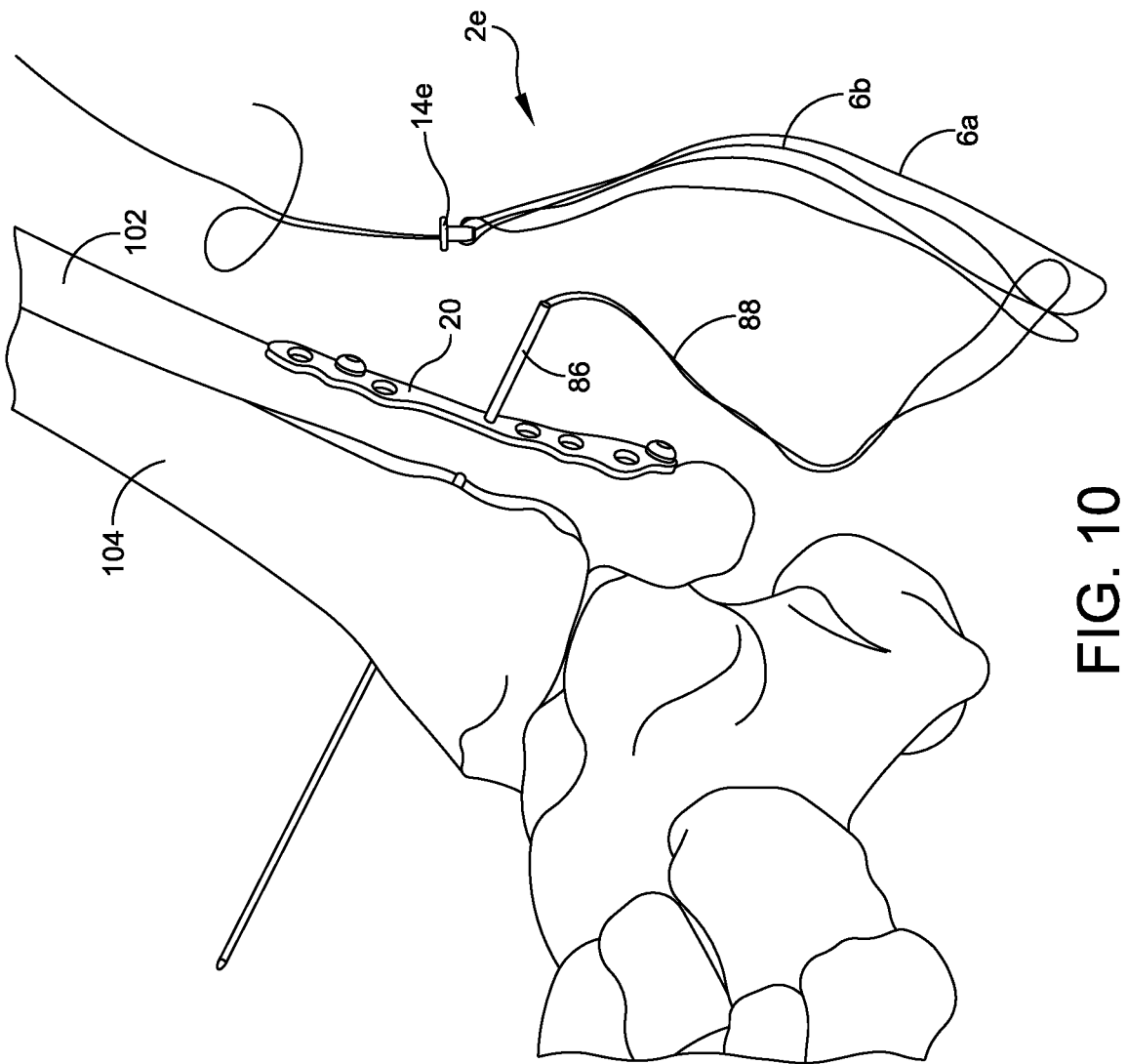
FIG. 10 illustrates the anchoring construct of FIG. 9 partially coupled to a first bone and a second bone through a bone plate, in accordance with some embodiments.

FIG. 10 illustrates an anchoring construct 2*e* partially coupled to a first bone 102 and a second bone 104 through a bone plate 20, in accordance with some embodiments. The anchoring construct 2*e* is similar to the anchoring construct 2*d* discussed in conjunction with FIG. 9, and similar description is not repeated herein. The needle 86 is inserted through a bone tunnel (see FIG. 1) defined by the first and second bones 102, 104. In some embodiments, the needle 86 is inserted into the bone tunnel through a button opening formed in the bone plate 20 (see FIGS. 11A-11C). In some embodiments, the bone plate 20 is coupled to the first bone 102 prior to insertion of the needle 86 through the bone tunnel. For example, in the illustrated embodiment, the bone plate 20 is coupled to the first bone 102 by a plurality of fasteners inserted through fastener holes defined by the bone plate. In other embodiments, the bone plate 20 is coupled to the bone by insertion and tightening of the anchoring construct 2*e*.

Figure 11A:
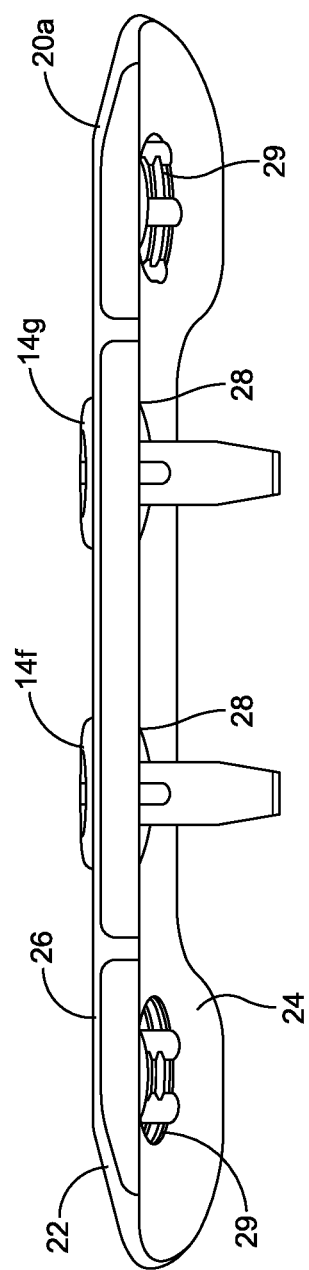
FIGS. 11A-11C illustrate knotless buttons at least partially inserted through one or more button holes in a bone plate, in accordance with some embodiments.
Figure 11B:
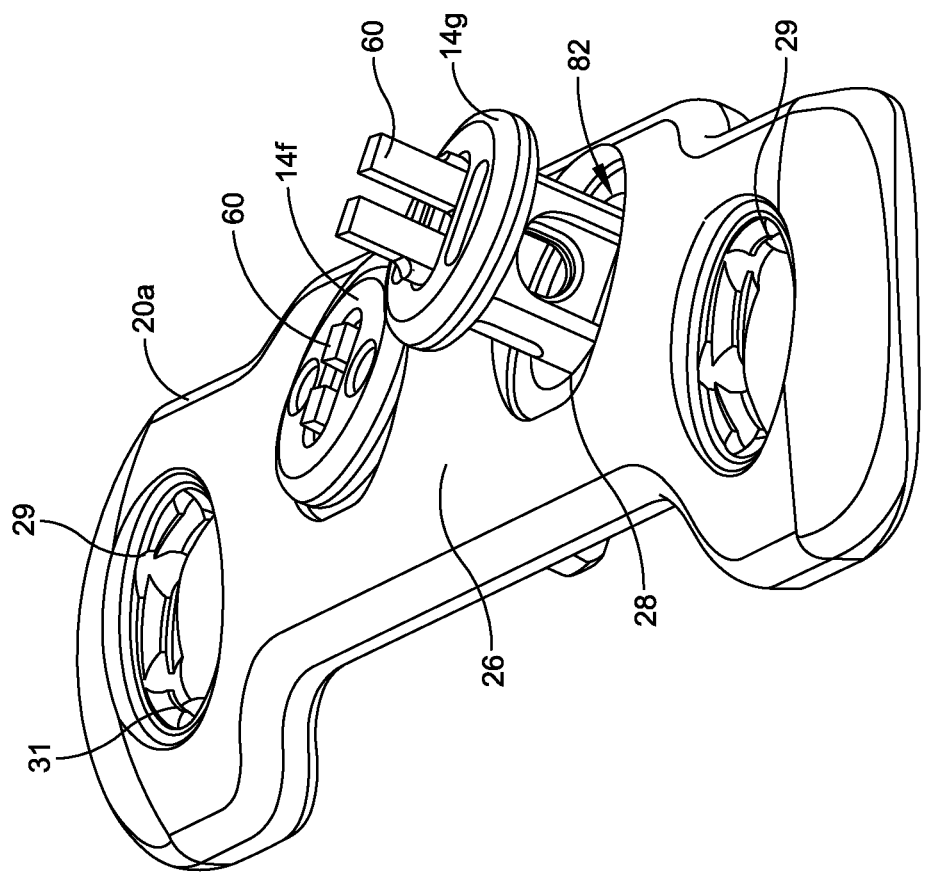
Figure 11C:
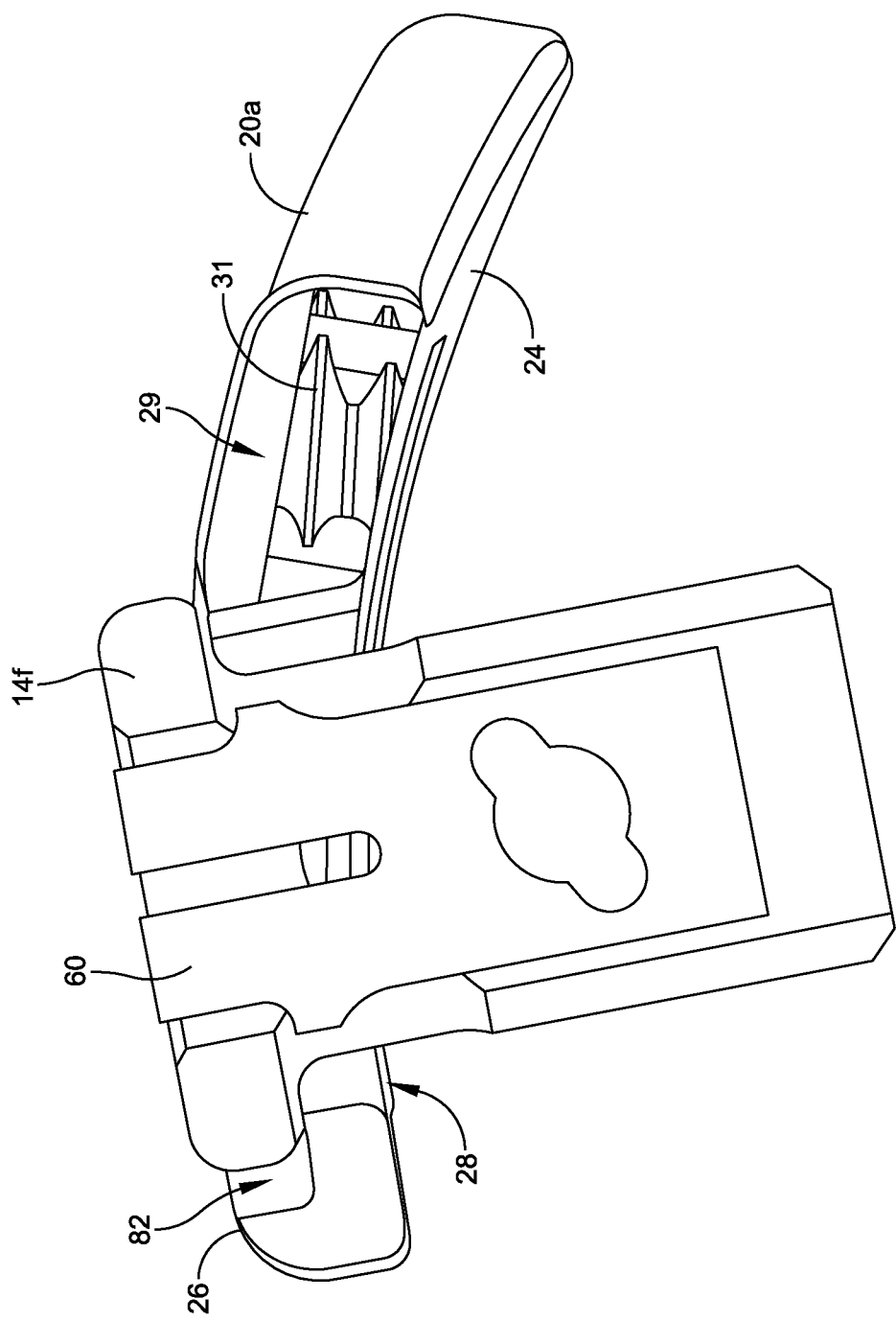

FIGS. 11A-11C illustrates a first knotless button 14*f* and a second knotless button 14*g* inserted through a button hole in a bone plate 20*a*, in accordance with some embodiments. Each of the knotless buttons 14*f*, 14*g* are inserted through button holes 28 extending from an outer surface 26 of the plate 20*a* to an inner surface 24 (or bone contact surface). In some embodiments, each of the button holes 28 define a countersink 82 (see FIG. 11B) such that the proximal end of the knotless buttons 14*f*, 14*g* are flush with the outer surface 26 when fully inserted into the button holes 28. In other embodiments, the knotless buttons 14*f*, 14*g* can extend at least partially above the outer surface 26. The bone plate 20*a* further defines a plurality of fastener holes 29 sized and configured for receiving a variable angle fastener therein. One or more variable angle fasteners can be used to anchor the bone plate 20*a* to a first bone (or bone fragment) prior to and/or after insertion of the knotless buttons 14*f*, 14*g* through the button holes 28. In some embodiments, the fastener holes 29 define at least a partial thread 31 configured to allow variable angle insertion of a fastener.

As shown in FIG. 11B, the knotless buttons 14f, 14g are inserted through the button holes 28 fully assembled (e.g., with the locking inserts 60 preinserted). As discussed above, one or more adjustable loops defined by a flexible strand can be tightened fix a position of a first bone (or bone fragment) and a second bone (or bone fragment). In some embodiments, tightening of the adjustable loops tightens the knotless buttons 14f, 14g against the bone plate 20a and temporarily anchors the plate 20a to a first bone.

FIG. 11C shows a cross-section of the bone plate 20a having the first knotless button 14f inserted into a first button hole 28. The first knotless button 14f can be inserted on an axis 99a that is perpendicular to the axis of curvature 99b of the bone plate 20a and/or can be inserted at an angle with respect to the axis of curvature 99b. In some embodiments, the axis 99a of the first knotless button 14f can intersect with an axis of a fastener hole 29. In such embodiments, a fastener is not inserted through the fastener hole 29.

Figure 12:
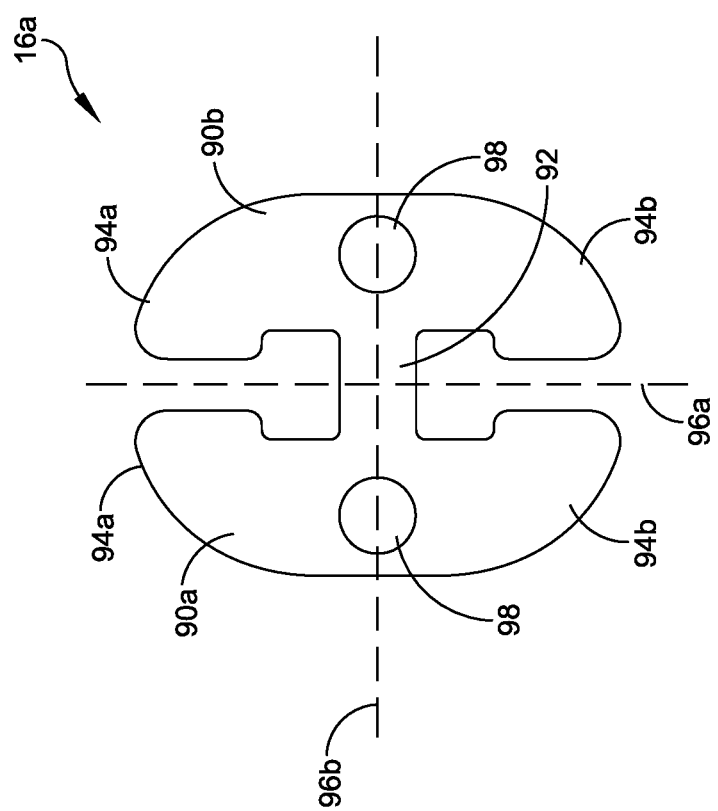
FIG. 12 illustrates a flat button configured to couple to an adjustable loop, in accordance with some embodiments.

FIG. 12 illustrates a flat button 16a, in accordance with some embodiments. The flat button 16a includes a first side 90a and a second side 90b coupled by a center post 92. Each of the first side 90a and the second side 90b include a first arm 94a and a second arm 94b extending at a predetermined arc from the center post 92. Each of the arms 94a, 94b are sized and configured to receive a portion of an adjustable loop 6 thereabout. The flat button 16a is configured to couple a distal end of an adjustable loop 6 to a second bone 104.

In some embodiments, the flat button 16a is sized and configured to be inserted through a bone tunnel 106 in a first configuration and to anchor a distal end of an adjustable loop 6 to a second bone in a second configuration. For example, in some embodiments, the flat button 16a has a first diameter along a first axis 96 less than a diameter of the bone tunnel 106. When the flat button 16a is oriented lengthwise with the first diameter perpendicular to the longitudinal axis of the bone tunnel 106, the flat button 16a can be inserted through the bone tunnel 106. After insertion, the flat button 16a is oriented such that a flat surface of the flat button 16a is positioned against the second bone 104 to anchor a second end of an adjustable loop 6. In other embodiments, the flat button 16a is coupled to the second end of the adjustable loop 6 after the adjustable loop 6 is inserted through the bone tunnel 106. In some embodiments, the flat button 16a defines a plurality of holes 98 sized and configured to receive an adjustable loop 6 and/or flexible strand 4 therethrough.

Figure 13:
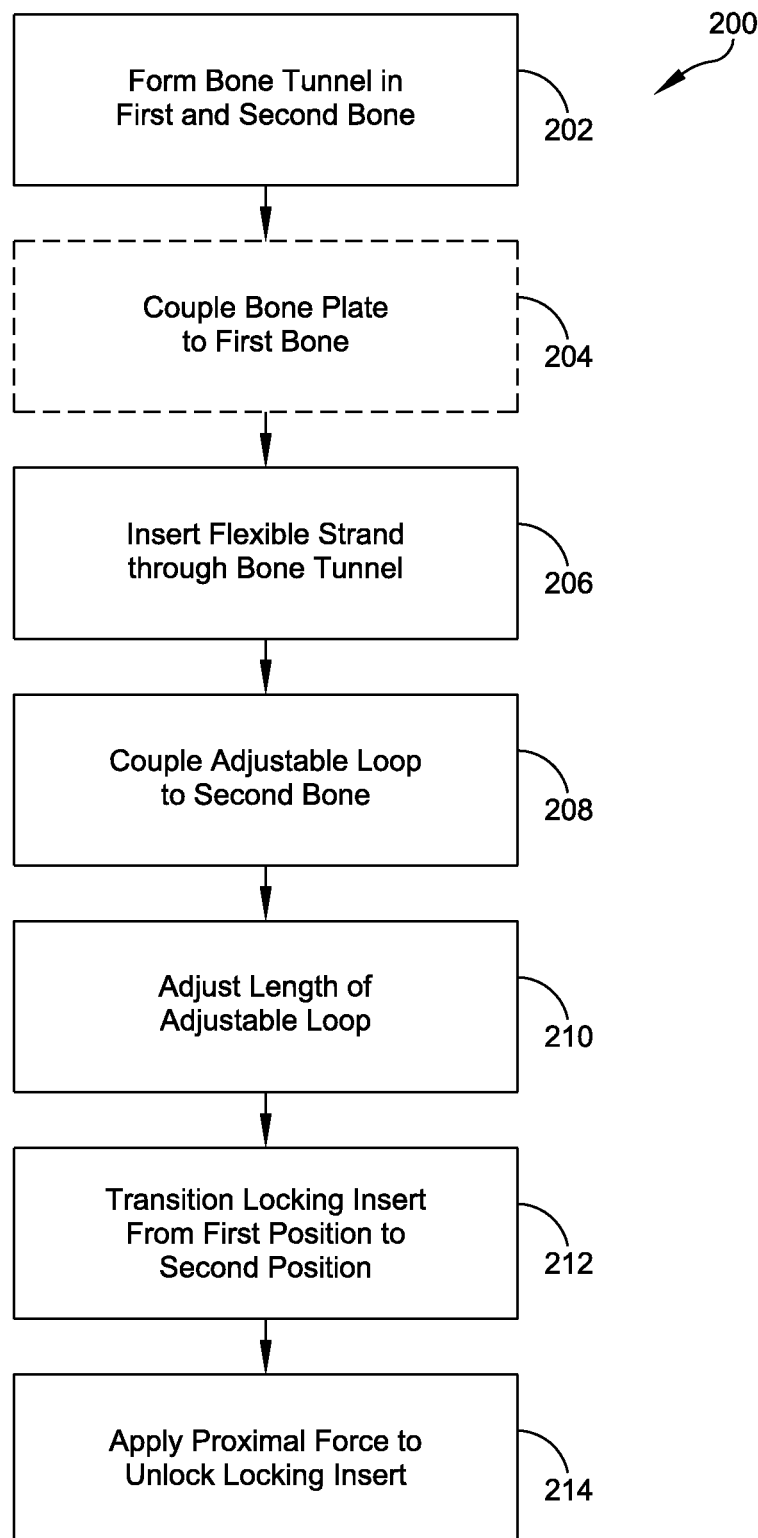
FIG. 13 illustrates a method for syndesmosis repair using an anchoring construct, in accordance with some embodiments.

FIG. 13 illustrates a method 200 of syndesmosis repair using an anchoring construct 2 as described herein, in accordance with some embodiments. At step 202, a bone tunnel 106 is formed through a first bone 102 and a second bone 104. The bone tunnel 106 can be formed using any suitable device, such as, for example, a drill, a k-wire, a needle, etc. In some embodiments, step 202 is performed simultaneously with one more later steps, such as step 206 discussed below.

At optional step 204, a bone plate 20 is coupled to the first bone 102. The bone plate 20 includes one or more knot capsule openings, and one or more fastener holes 74a-74d. The bone plate 20 can be coupled to the first bone 102 using one or more fasteners 76 inserted through one or more of the fastener holes 74a-74d. In other embodiments, the bone plate 20 can be temporarily coupled to the first bone 102 by, for example, a k-wire or other temporary fixation device.

At step 206, an anchor construct 2 is coupled to the first bone 102 and the second bone 104. The anchor construct 2 is coupled to the first and second bones 102, 104 by inserting a flexible strand 4 defining at least one adjustable loop 6 through the bone tunnel 106. In some embodiments, a distal end 10 of the adjustable loop 6 is coupled to a flat button 16. The flat button 16 can be coupled to the distal end 10 of the adjustable loop 6 prior to insertion of the adjustable loop 6 through the bone tunnel 106. In such embodiments, the flat button 16 is sized and configured for insertion through the bone tunnel 106 in at least a first configuration and is sized and configured to prevent movement through the bone tunnel 106 in a second configuration. In some embodiments, the flat button 16 is coupled to the distal end 10 of the adjustable loop 6 after insertion of the adjustable loop 6 through the bone tunnel 106.

At step 208, the distal end 10 of the adjustable loop 6 is coupled to the second bone. For example, in some embodiments, the flat button 16 is coupled to the adjustable loop 6 and positioned against an outer edge of the second bone 104.

At step 210, the adjustable loop 6 is shortened to reduce the distance between the first bone 102 and the second bone 104 to a predetermined spacing. The adjustable loop 6 can be shortened by, for example, an adjustment portion 12 extending through a first opening 42 formed in a proximal cap 34a of a knotless button 14. Applying a proximal force to the adjustment portion 12 shortens the adjustable loop 6. It will be appreciated that additional methods can be used to shorten the adjustable loop 6, such as, for example, pulling the proximal end 8 of the adjustable loop 6 through one or more openings of the knot capsule 14 and manually adjusting the length of the adjustable loop 6.

At step 212, a locking insert 60 positioned within an internal cavity 48 defined by the knotless button 14 is transitioned from a first position to a second position to lock the adjustable loop 6 at the selected length. In some embodiments, the locking insert 60 automatically transitions from the first position to the second position when the adjustable loop 6 is shortened to a predetermined length.

At optional step 214, a proximal force can be applied to the locking insert 60 by a release loop 54 to transition the locking insert 60 from the second position to the first position. The method can optionally return to step 210 to further adjust the length of the adjustable loop 6. The method 200 then returns to step 212 to lock the locking insert 60 when the adjustable loop 6 is adjusted to a second predetermined length.

In various embodiments, a knotless button includes a body defining a proximal portion and a distal portion. The body further defines an internal cavity and a first loop opening extending from the internal cavity to an outer surface of the body. A locking insert is slideably positioned within the internal cavity. The locking insert defines a second loop opening extending from a first side of the locking insert to a second side of the locking insert. The locking insert is slideably moveable from a first position to a second position within the internal cavity. A flexible strand defines a first adjustable loop extending through the first loop opening and the second loop opening. The locking insert is slideably moveable from a first position configured to allow adjustment of the first adjustable loop to a second position configured to lock the first adjustable loop.

In some embodiments, the flexible strand extends from a first side of the locking insert to a second side of the locking insert through the second loop opening, from the second side of the locking insert to the first side of the locking insert beneath a distal edge of the locking insert, and from the first side of the locking insert to the second side of the locking insert through the second suture opening. In some embodiments, the first adjustable loop is configured to apply a force to the locking insert. The force applied by the first adjustable loop transitions the locking insert from the first position to the second position.

In some embodiments, the locking cavity defines at least one first locking feature and the locking insert comprises at least one second locking feature. The first locking feature is configured to interface with the second locking feature to maintain the locking insert in a fixed position with respect to the body. The at least one first locking feature can be a slot and the at least one second locking feature can be a tab.

In some embodiments, the body is tapered at a distal end portion. The body can further defines a second suture opening extending from the internal cavity to the outer surface of the body. The distal portion of the body is sized and configured to be received within a bone tunnel.

In some embodiments, a knotless button includes a body having a proximal portion and a distal portion. The body defines an internal cavity including at least one first locking feature. A locking insert is slideably positioned within the internal cavity. The locking insert defines a first loop opening extending from a first side to a second side. The locking insert is slideably moveable from a first position to a second position and is configured to receive a flexible strand defining a first adjustable loop through the first loop opening. The locking insert includes at least one second locking feature configured to selectively couple to the first locking feature to prevent movement of the locking insert with respect to the body.

In some embodiments, the first loop extends from a first side of the locking insert to a second side of the locking insert through the first loop opening, from the second side of the locking insert to the first side of the locking insert beneath a distal edge of the locking insert, and from the first side of the locking insert to the second side of the locking insert through the first suture opening. The adjustable loop can apply a predetermined force to the locking insert when the adjustable loop has a predetermined length. The force applied by the adjustable loop transitions the locking insert from the first position to the second position.

In some embodiments, the at least one first locking feature is a slot and the at least one second locking feature is a tab. The body can be tapered at the distal portion. The distal portion of the body is sized and configured to be received within a bone tunnel.

In some embodiments, a release strand is coupled to the locking insert. The release strand extends proximally from the locking insert and is configured to selectively release the at least one first locking feature and the at least one second locking feature.

In some embodiments, a method of coupling a first bone and a second bone is disclosed. The method includes forming a bone tunnel through a first bone and a second bone. A knotless button is inserted at least partially through the bone tunnel. The knotless button includes a body having a proximal portion and a distal portion and further defining an internal cavity and a first loop opening, a locking insert slideably positioned within the internal cavity and defining a second loop opening extending from a first side to a second side, and a flexible strand defining a first adjustable loop extending through the first loop opening and the second loop opening. The first adjustable loop is coupled to the second bone and is adjusted to position the first bone and the second bone. Adjusting the first adjustable loop slideably transitions the locking insert from a first position in which the first adjustable loop is adjustable to a second position in which the first adjustable loop is locked.

In some embodiments, the method further includes locking the locking insert with respect to the body. The internal cavity defines at least one first locking feature and the locking insert defines at least one second locking feature. The locking insert is locked by coupling the at least one first locking feature and the at least one second locking feature.

In some embodiments, the method further includes uncoupling the at least one first locking feature and the at least one second locking feature to transition the locking insert from the second position to the first position. The at least one first locking feature and the at least one second locking feature are released by a proximal force applied by a release loop coupled to the locking insert. The first adjustable loop is adjusted and locking insert is transitioned from the first position to the second position.

In some embodiments, the knotless button is inserted through a hole defined in a bone plate prior to inserting the knotless button into the bone tunnel. The bone plate defines a body having an outer surface and a bone contact surface. The bone plate is maintained in a fixed position with respect to the first bone.

In some embodiments, coupling the first adjustable loop to the second bone comprises coupling a flat button to the second bone. The flat button is coupled to a distal end of the first adjustable loop and includes at least one dimension greater than a diameter of the bone tunnel.

Although the subject matter has been described in terms of exemplary embodiments, it is not limited thereto. Rather, the appended claims should be construed broadly, to include other variants and embodiments, which may be made by those skilled in the art.

What is claimed is:
1. A knotless button, comprising:
a body defining a proximal portion and a distal portion, the body defining an internal cavity and a first loop opening extending from the internal cavity to an outer surface of the body;
a locking insert slideably positioned within the internal cavity, the locking insert defining a second loop opening extending from a first side of the locking insert to a second side of the locking insert, and wherein the locking insert is slideably moveable from a first position to a second position within the internal cavity; and
a flexible strand defining a first adjustable loop extending through the first loop opening from a first side of the locking insert to a second side of the locking insert, through the second loop opening, and beneath a distal edge of the locking insert, wherein the locking insert is slideably moveable from a first position configured to allow adjustment of the first adjustable loop to a second position configured to lock the first adjustable loop so that the first adjustable loop applies a force to the locking insert to thereby transition the locking insert from the first position to the second position.

2. The knotless button of claim 1, wherein the locking insert defines at least one first locking feature and the locking cavity defines at least one second locking feature, wherein the first locking feature is configured to interface with the second locking feature to maintain the locking insert in a fixed position with respect to the body.

3. The knotless button of claim 2, wherein the at least one first locking feature is a tab and the at least one second locking feature is a slot.

4. The knotless button of claim 1, wherein the body is tapered at a distal end portion.

5. The knotless button of claim 1, wherein the body further defines a second suture opening extending from the internal cavity through the body.

6. The knotless button of claim 1, wherein the distal portion of the body is sized and configured to be received within a bone tunnel.

7. A method of coupling a first bone and a second bone, comprising:
forming a bone tunnel through a first bone and a second bone;
inserting a knotless button at least partially through the bone tunnel, the knotless button comprising a body defining a proximal portion and a distal portion, the distal portion defining an internal cavity and a first loop opening, a locking insert slideably positioned within the internal cavity and defining a second loop opening extending from a first side to a second side, and a flexible strand defining a first adjustable loop extending through the first loop opening and the second loop opening and beneath a distal edge of the locking insert;
coupling the first adjustable loop to the second bone; and
adjusting the first adjustable loop to position the first bone and the second bone, wherein adjusting the first adjustable loop to apply a force that slideably transitions the locking insert from a first position in which the first adjustable loop is adjustable to a second position in which the first adjustable loop is locked.

8. The method of claim 7, further comprising locking the locking insert with respect to the body, wherein the internal cavity defines at least one first locking feature and the locking insert defines at least one second locking feature, and wherein the locking insert is locked by coupling the at least one first locking feature and the at least one second locking feature.

9. The method of claim 8, further comprising:
uncoupling the at least one first locking feature and the at least one second locking feature to transition the locking insert from the second position to the first position, wherein the at least one first locking feature and the at least one second locking feature are released by a proximal force applied by a release loop coupled to the locking insert;
adjusting the first adjustable loop; and
transitioning the locking insert from the first position to the second position.

10. The method of claim 7, further comprising inserting the knotless button through a hole defined in a bone plate prior to inserting the knotless button into the bone tunnel, wherein the bone plate defines a body having an outer surface and a bone contact surface, and wherein the bone plate is maintained in a fixed position with respect to the first bone.

11. The method of claim 7, wherein coupling the first adjustable loop to the second bone comprises coupling a flat button to the second bone, wherein the flat button is coupled to a distal end of the first adjustable loop, and wherein the flat button includes at least one dimension greater than a diameter of the bone tunnel.

* * * * *